(12) United States Patent
Bove et al.

(10) Patent No.: US 6,652,446 B1
(45) Date of Patent: Nov. 25, 2003

(54) DEEP HEATING MAGNETIC WRAP FOR JOINTS AND TISSUE

(76) Inventors: Anthony Bove, 6 Northwind Dr., Port Jefferson, NY (US) 11177; Vincent Ardizzone, 46 Grandview Blvd., Miller Place, NY (US) 11764

( * ) Notice: Subject to any disclaimer, the term of this patent is extended or adjusted under 35 U.S.C. 154(b) by 0 days.

(21) Appl. No.: 09/909,674

(22) Filed: Jul. 19, 2001

Related U.S. Application Data

(63) Continuation-in-part of application No. 09/038,508, filed on Mar. 10, 1998, now abandoned, which is a continuation-in-part of application No. 08/911,950, filed on Aug. 15, 1997, now Pat. No. 6,293,900, which is a continuation-in-part of application No. 08/678,348, filed on Jul. 11, 1996, now Pat. No. 5,871,438, which is a continuation of application No. 08/573,390, filed on Dec. 15, 1995, now Pat. No. 5,538,495, which is a continuation of application No. 08/427,733, filed on Apr. 24, 1995, now Pat. No. 5,514,072, which is a continuation of application No. 08/276,876, filed on Jul. 18, 1994, now abandoned, which is a continuation of application No. 08/158,607, filed on Nov. 29, 1993, now abandoned, which is a continuation of application No. 07/990,927, filed on Dec. 14, 1992, now Pat. No. 5,277,692, which is a continuation of application No. 07/823,149, filed on Jan. 21, 1992, now abandoned, and a continuation-in-part of application No. 08/565,826, filed on Dec. 1, 1995, now abandoned.

(51) Int. Cl.[7] .................................... A61N 1/00
(52) U.S. Cl. ........................................... 600/15
(58) Field of Search ........................ 600/9–15

(56) References Cited

U.S. PATENT DOCUMENTS

| | | | | |
|---|---|---|---|---|
| 3,943,912 A | * | 3/1976 | Nakayama | 600/15 |
| 4,489,711 A | | 12/1984 | Latzke | 128/1.3 |
| 4,549,532 A | * | 10/1985 | Baermann | 428/40.9 |
| 4,587,956 A | * | 5/1986 | Griffin et al. | 600/15 |
| 4,925,134 A | | 5/1990 | Keller et al. | 244/158 A |
| 5,017,185 A | | 5/1991 | Baermann | 600/15 |
| 5,122,291 A | | 6/1992 | Wolff et al. | 252/62 |
| 5,304,111 A | | 4/1994 | Mitsuno et al. | 600/9 |
| 5,389,061 A | * | 2/1995 | Nor | 54/82 |
| 5,538,495 A | | 7/1996 | Ardizzone | 600/9 |
| 5,626,951 A | | 5/1997 | Hogenson | 442/262 |
| 5,720,046 A | * | 2/1998 | Lopez et al. | 2/159 |
| 5,738,624 A | * | 4/1998 | Zablotsky et al. | 600/15 |
| 5,800,905 A | | 9/1998 | Sheridan et al. | 428/157 |
| 5,807,233 A | | 9/1998 | Sakuma et al. | 600/15 |
| 5,811,168 A | | 9/1998 | Rasky et al. | 428/102 |
| 5,882,292 A | * | 3/1999 | Miyaguchi | 600/15 |
| 6,126,588 A | * | 10/2000 | Flamant et al. | 600/15 |
| 6,293,900 B1 | * | 9/2001 | Bove et al. | 600/15 |

* cited by examiner

Primary Examiner—John P. Lacyk
(74) Attorney, Agent, or Firm—Cislo & Thomas LLP

(57) ABSTRACT

Flexible and elastic magnetic joint wraps incorporate superstrong magnets with alternating polarities and incorporate bio-ceramic fibers to provide enhanced magnetotherapeutic and far-infrared effects. Magnetotherapeutic joint wraps that are flexible and elastic incorporate superstrong magnets as well as far-infrared emitters in an attachably detachable manner so as to provide magnetotherapy and far-infrared therapy to joints and surrounding tissues. Neoprene or the like may incorporate superstrong magnets such as those based on iron (magnetic ferrite) or neodymium (particularly neodymium-iron-boron (NdFeB)) in order to provide superstrong static magnetism by which magnetotherapy may be effected. Elements that are generally oppositely opposed serve to detachably attach portions of the magnetic wrap to one another so that the magnetic joint wrap may conform to the local shape and form of the area adjacent the joint. Such attachment elements may include VELCRO® hook and loop fasteners as well as buttons, snaps, and the like. The superstrong magnets are constructed such that they may be incorporated in flexible and elastic materials such as neoprene. This provides means by which a magnetic wrap may tautly wrap around the joint and adjacent area when attached by the attachment elements. A soft cover may incorporate or cover bio-ceramic fibers which provide far-infrared treatment for the adjacent tissues and/or joints. Additionally, eye and face masks may incorporate the superstrong magnets and bio-ceramic fibers as used in the deep heating magnetic joint wrap of the present invention to good advantage.

24 Claims, 10 Drawing Sheets

```
┌─────────────────────────────────────────────────────┐
│ 208                                                 │
│     COMBINED STRETCH FABRIC AND BIO-CERAMIC FIBER   │
└─────────────────────────────────────────────────────┘
┌─────────────────────────────────────────────────────┐
│ 200                                                 │
│            FLEXIBLE MAGNETIC SHEET                  │
└─────────────────────────────────────────────────────┘
    ┌─────────────────────────────────────────────────┐
    │ 202           BIO-CERAMIC FIBERS                │
    └─────────────────────────────────────────────────┘
    ┌─────────────────────────────────────────────────┐
    │ 204            STRETCH FABRIC                   │
    └─────────────────────────────────────────────────┘
```

| N | S | N | S | N |
|---|---|---|---|---|
| S | N | S | N | S |
| N | S | N | S | N |
| S | N | S | N | S |
| N | S | N | S | N |

FIG. 10

DEEP HEATING MAGNETIC WRAP FOR JOINTS AND TISSUE

CROSS-REFERENCES TO RELATED APPLICATIONS

This patent application is a continuation-in-part of U.S. patent application Ser. No. 09/038,508 filed Mar. 10, 1998 now abandoned by the same inventors for a Magnetic Wrap for Joints; which is a continuation-in-part application of U.S. patent application Ser. No. 08/911,950 filed Aug. 15, 1997 now U.S. Pat. No. 6,293,900; which is a continuation-in-part application of U.S. patent application Ser. No. 08/678,348 filed Jul. 11, 1996, now U.S. Pat. No. 5,871,438; which is a continuation of application Ser. No. 08/573,390, filed Dec. 15, 1995, now U.S. Pat. No. 5,538,495; which is a continuation of application Ser. No. 08/427,733, filed Apr. 24, 1995, now U.S. Pat. No. 5,514,072; which is a continuation of application Ser. No. 08/276,876, filed Jul. 18, 1994, now abandoned; which is a continuation of application Ser. No. 08/158,607, filed Nov. 29, 1993, now abandoned; which is a continuation of application Ser. No. 07/990,927, filed Dec. 14, 1992, now U.S. Pat. No. 5,277,692; which is a continuation of application Ser. No. 07/823,149, filed Jan. 21, 1992, now abandoned. This application is also a continuation-in-part of U.S. patent application Ser. No. 08/565,826 filed Dec. 1, 1995, now abandoned. The contents of all related applications of which the present application is a divisional, continuation, continuation-in-part, or otherwise from which this application is related are incorporated herein by this reference thereto.

BACKGROUND OF THE INVENTION

1. Field of the Invention

This invention relates to magnetotherapeutic devices, and more particularly to muscle and/or joint wraps incorporating static magnetic field generators in the form of magnets used in conjunction with bio-ceramic fibers to provide simultaneous magnetotherapy and far-infrared treatment to adjacent tissues.

2. Description of the Related Art

Magnetotherapy uses magnetic fields to provide therapeutic and restorative treatment to limbs, organs, and other parts of the body. Generally, one means by which magnetotherapy may be achieved is by bringing a magnet or a series of magnets into close proximity with the affected body part or organ of interest. As is known according to Faraday's Law of Magnetic Induction, as well as the Hall Effect, charged particles experience a force acting on them when they move through a magnetic field in a perpendicular direction. Since human blood is replete with ions and electrolytes, it has many charged molecules, particles, and the like which experience a force, including an aligning force, when moving through a magnetic field. When exposed and caused to travel through a magnetic field, such ions and electrolytes may generate heat, causing the associated blood vessel to widen. The widening of the blood vessel would then allow increased volumes of blood to flow through the blood vessel.

Magnetotherapy is known in the art and used to provide relief for aches and pains by the application of magnetics, particularly strong magnets, to the affected area of the body. Due to the Hall effect and otherwise, the travel of fluids in the body past areas influenced by the magnetotherapeutic magnet or subject to magnetotherapy causes charges, such as those in electrolytes, to undergo forces and gently churn the fluids (such as blood, lymph, and plasma) in which they travel. Such innate activity of the bodily fluids may serve to stimulate a number of body processes.

Polar molecules (such as water) also respond to magnetic fields in a manner similar to that for charged molecules. Additional therapeutic or restorative effects might arise through the alignment of polar molecules as they pass through the magnetic field. When subject to a magnetic field, polar molecules rotate to align themselves with the field. Such alignment would alternate with the magnetic polarity as the polar molecules traveled through different regions of such magnetic polarity. The mechanical motion of the rotation of such polar molecules might also cause heating and the like and would also stimulate, mix, or agitate the blood in a gentle manner, causing it to gently churn. Such mixing of the blood at the molecular level may cause it to more easily recognize foreign matter. By recognizing foreign matter, the blood and/or immune system may be able to more readily address such foreign matter.

Several patents are known having various designs for the alternation of magnets of different polarity to provide spatially diverse magnetic fields. The patent to Latzke (U.S. Pat. No. 4,489,711 issued Dec. 25, 1984) and the patents to Ardizzone (U.S. Pat. No. 5,277,692 issued Jan. 11, 1994; U.S. Pat. No. 5,514,072 issued May 7, 1996; and U.S. Pat. No. 5,538,495 issued Jul. 23, 1996) all disclose a variety of magnetic plaster and magnetic pads having certain magnetic geometries in order to achieve spatially varying magnetic fields through the use of magnets.

In the past, the only way to offer or provide both mechanical support and magnetic therapy was to insert magnets between a brace and the associated body joint. Recently, stronger static magnetic materials have become more readily available in the commercial market. Particularly, permanent magnets incorporating the element neodymium (atomic number 60) provide strong magnetic fields at common temperatures (below 120° F./50° C.). Such magnets can be incorporated into flexible fabrics or the like to provide a flexible material suitable for wrapping around joints. By using flexible and/or elastic materials such as neoprene, a magnetotherapeutic joint wrap previously unseen in the art could be realized.

While certain portions of the human body have been emphasized as being subject to the use of magnetotherapeutic devices, it remains to be seen in the art to provide such magnetotherapy in the form of a wrap or the like for joints. Additionally, strong, magnetic material used in such joint wraps could be used in an eye or face mask incorporating such magnetotherapeutic elements. It can be seen, therefore, that it would be of some advantage to provide magnetotherapeutic aid to a person's joints, eyes, and/or face, particularly while the person rests or sleeps as such magnetotherapeutic treatment could then be effected for a period of several hours without interfering with a person's daily and ongoing activities.

Furthermore, recent developments in the art have found that human tissue is advantageously susceptible to light in the far-infrared range. Infrared light waves are generally known as heat waves and serve to warm objects thermally upon which such infra-red waves come into contact or shine upon. Light waves in the far-infrared may have a tendency to penetrate more deeply into the tissue and serve to stimulate such tissue accordingly.

The present invention provides means by which such effects may be combined into a conveniently applied unit, such that fluids coursing through the body may be simultaneously stimulated by magnetotherapy while the deeper tissues of the body may be subject to far-infrared stimulation in combination with such magnetotherapy.

SUMMARY OF THE INVENTION

The present invention provides a magnetic wrap incorporating bio-ceramic fibers by which coordinated magnetotherapy and far-infrared treatment may be simultaneously applied to joints and adjacent tissues. A sheet of magnetic material, preferably of a highly magnetic material, is both flexible and elastic. Preferably, this highly magnetic flexible sheet has alternating polarity along its course so that travel in any direction provides alternating polarity. Strong magnets in the shapes of triangles, squares, and/or series of concentric circles may be used to provide such alternating polarity.

In the preferred embodiment, the strong source of magnetism incorporated into the magnetic wrap for joints of the present invention may arise from the use of neodymium-based magnets which may be incorporated into neoprene or the like. By providing a flexibly elastic highly magnetic sheet of material having alternating magnetic polarities, a joint about which such a magnetic sheet is wrapped becomes subject to significant magnetotherapy. Magnetic ferrite may also be used in the place of the neodymium-based magnets.

In order to better accommodate the joint, an aperture may be cut or fashioned in the sheet of magnetic material so as to accommodate the joint. Such an aperture may accommodate a joint such as a knee, elbow, shoulder, or the like.

Additionally, in order to hold the magnetic wrap for joints of the present invention in place, attachments or attachment elements holding the magnetic sheet in place may be strategically positioned upon the sheet and may take the form such as VELCRO® hook and fasteners, or the like. Buttons, snaps, and other fasteners may also be used to good advantage.

Additionally, beyond the use of strong, neodymium-based magnetics in alternating polarity configurations for use in joint wraps, face masks and eye masks may also incorporate such strong magnets so as to provide greater magnetotherapeutic effect for adjacent tissues. Such face masks have been disclosed in part in prior U.S. patent application Ser. No. 08/911,950 filed Aug. 15, 1997 which is incorporated herein by this reference thereto.

Such magnetotherapy is provided in conjunction with tissue treatment by far-infrared waves as bio-ceramic fibers are provided in conjunction with the supplied magnetotherapy.

Bio-ceramic fibers are able to radiate or provide far-infrared waves at room temperature and when heated to a body temperature of approximately 98.6° F. As magnetotherapy requires the application of the magnetism to tissue, by holding the present invention as a magnetotherapeutic device against the body, the accompanying bio-ceramic fibers are warmed by the body and allow the device to provide both magnetotherapy and far-infrared treatment to the adjacent tissue. Bio-ceramics and other far-infrared emitters have been used in conjunction with magnetotherapeutic devices. U.S. Provisional Patent Application Ser. No. 60/143,809 filed Jul. 14, 1999 by the same inventors sets forth a far-infrared magnetotherapeutic disk. Said provisional patent application is incorporated herein by this reference to it.

The bio-ceramic fibers may be woven into a surface cover or other structure overlying the flexible magnetic sheet. Backing the bio-ceramic fiber mat or cloth may be the neodymium (Nd) or other strong magnets.

OBJECTS OF THE INVENTION

It is an object of the present invention to provide a magnetotherapeutic wrap for joints.

It is another object of the present invention to provide highly magnetic magnetotherapy for such joints.

It is an additional object of the present invention to provide strong magnetotherapeutic joint wraps for joints with such joint wraps having alternating magnetic polarity.

It is yet another object of the present invention to provide face and eye masks incorporating strong magnets so as to apply magnetotherapeutic treatment upon adjacent tissues.

It is an object of the present invention to provide magnetotherapy in conjunction with far-infrared treatment of body tissues.

It is another object of the present invention to provide such magnetotherapy by means of a strong magnet.

It is yet another object of the present invention to provide such far-infrared treatment by providing bio-ceramic fibers that radiate, transmit, emit, or provide far-infrared waves at least when brought to body temperature.

It is yet another object of the present invention to combine magnetotherapy and far-infrared wave treatment in an integral and consolidated device that is convenient to apply and use.

These and other objects of the present invention will be apparent from a review of the following specification and accompanying drawings.

BRIEF DESCRIPTION OF THE DRAWINGS

Figure 10:
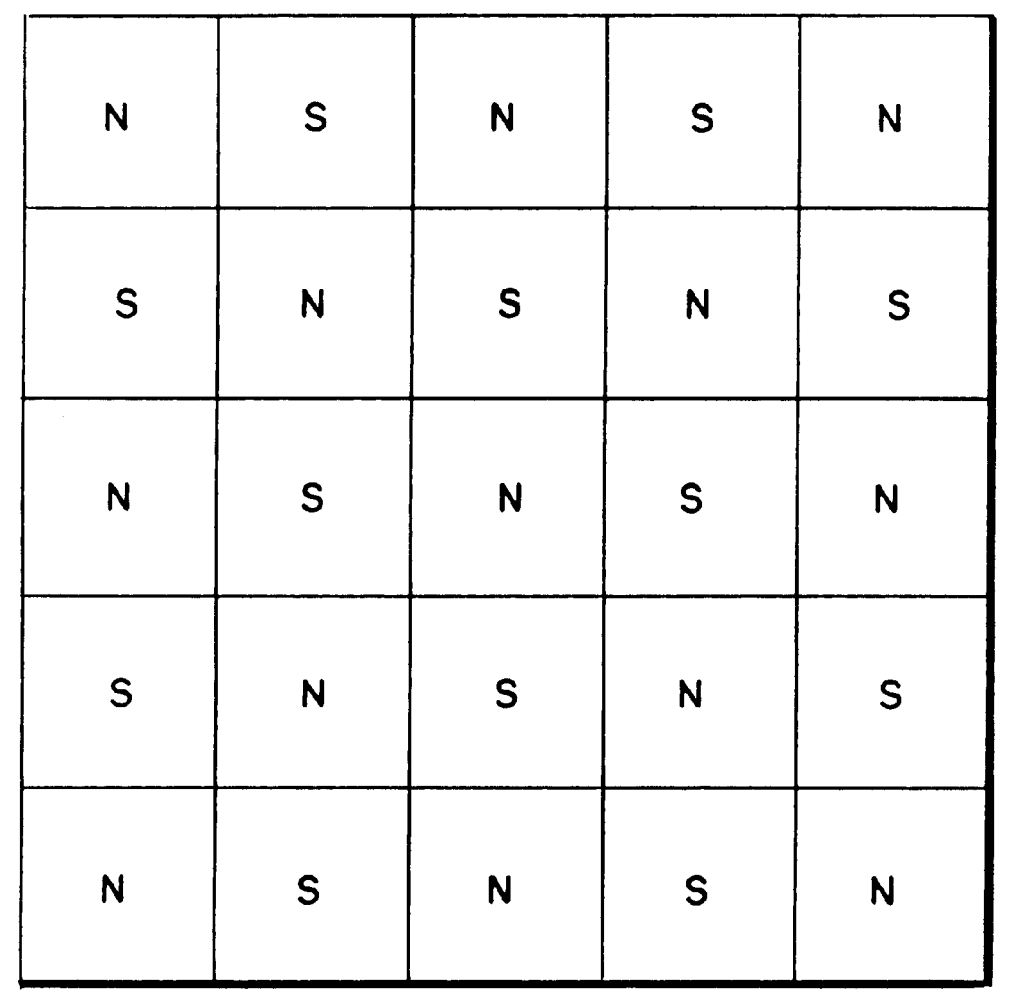

FIGS. 9 and 10 show a checkerboard-type magnet configuration for use in the present invention.

DESCRIPTION OF THE PREFERRED EMBODIMENT(S)

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

The present invention is directed mainly towards a magnetic wrap for joints by which magnetotherapy and far-infrared therapy may be applied to joints and the adjacent tissue without unduly interfering with the operation of the associated joint. Additionally, strong and alternating static magnets may be used not only in such magnetic wraps for joints, but also in eye masks and face masks. Coupled with the far-infrared activity of the accompanying bio-ceramic fibers, enhanced therapeutic stimulation may be provided for injured or aching joints or tissues.

Figure 1:
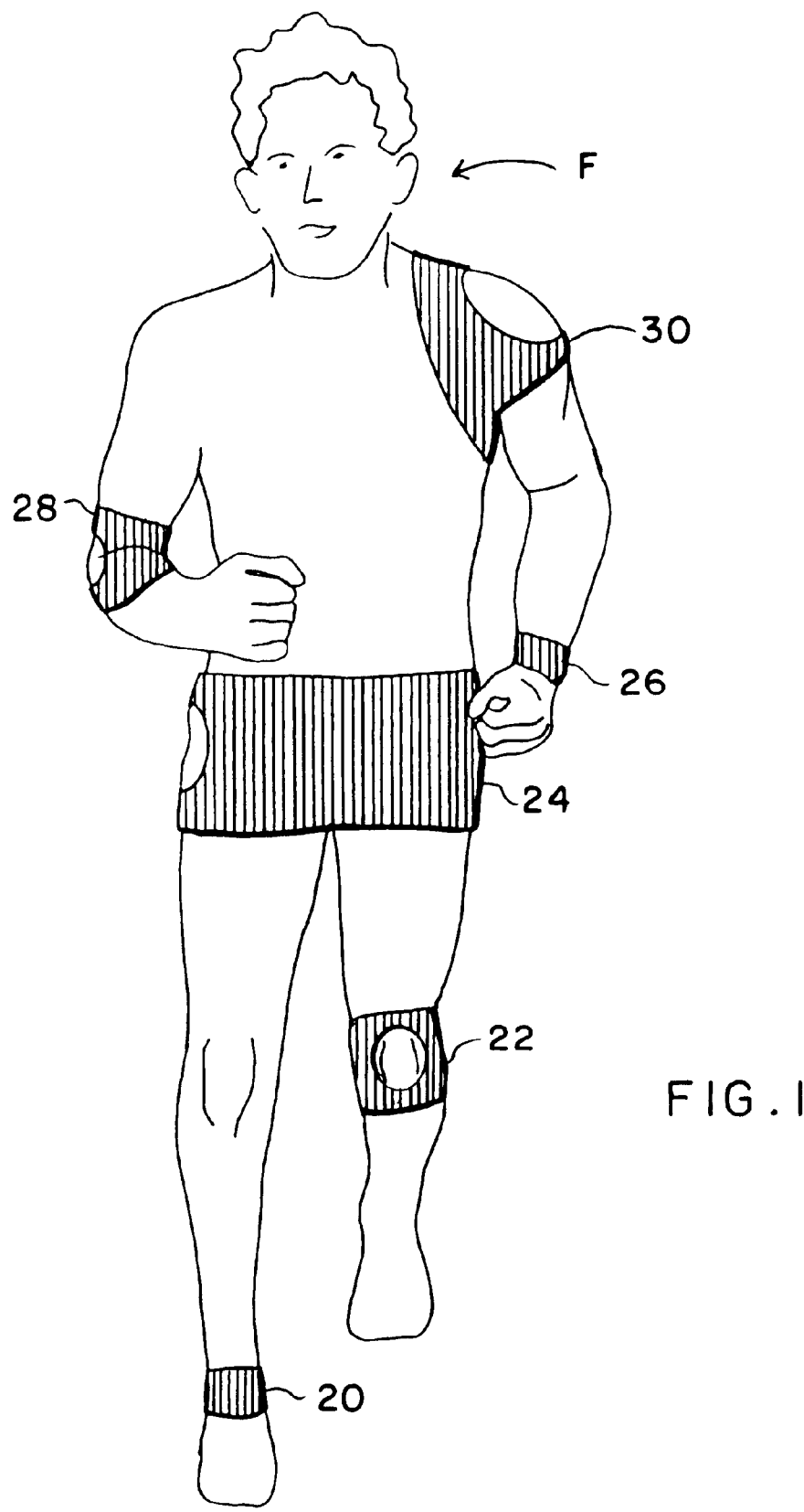
FIG. 1 shows a human figure bearing several embodiments of the magnetic wrap for joints of the present invention including an ankle wrap, a knee wrap, a hip wrap, a wrist wrap, an elbow wrap, and a shoulder wrap.

As shown in FIG. 1, a Figure F is shown wearing several of the different embodiments of the present invention. The far-infrared magnetic joint wraps (FIG. 2 et seq.) of the present invention may take several forms in order to accommodate several different types of joints. As shown in FIG. 1, the Figure F is bearing an ankle wrap 20, a knee wrap 22, a hip wrap 24, a wrist wrap 26, an elbow wrap 28, and a shoulder wrap 30. Neck wraps or the like might be similar to a hip wrap 24 or the like in order to provide a magneto-therapeutic collar or the like. Such neck wraps might have a descending extension that covers a top end of the spine or all or part of the cervical vertebrae.

As shown in FIG. 1, the magnetic joint wraps often incorporate apertures or the like in order to accommodate the joint associated with the adjacent tissue. Each of the magnetic joint wraps incorporate far-infrared emitters to provide additional therapy in the form of far-infrared treatment.

Figure 2:
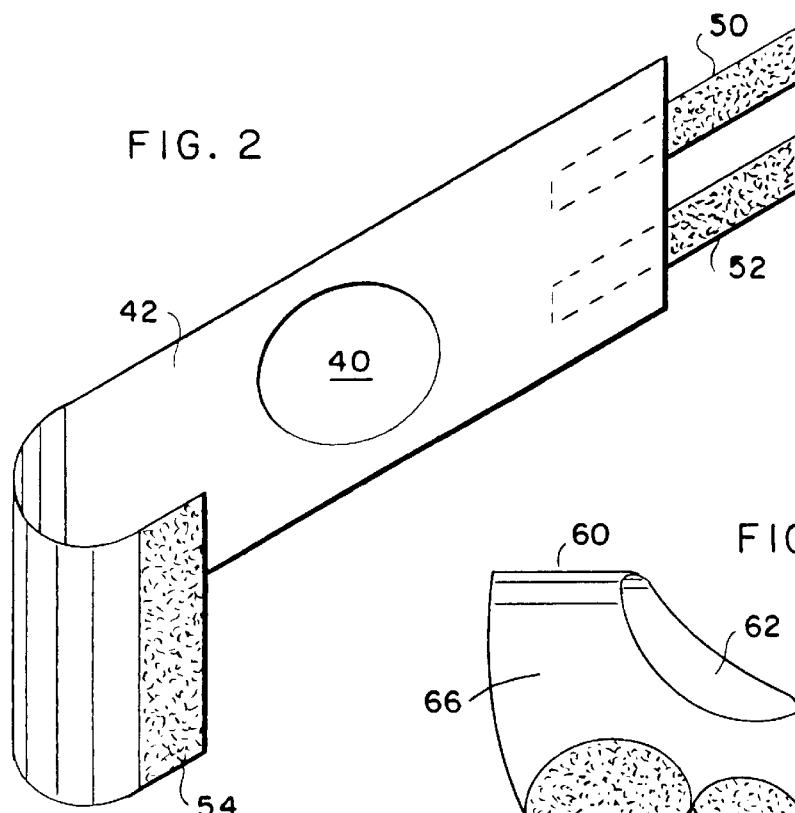
FIG. 2 shows an embodiment of a hip, wrist or ankle wrap constructed according to the present invention.

In FIG. 2, a hip or wrist wrap configuration is shown indicating such an aperture 40. The aperture 40 is strategically located so that upon wrapping the magnetic joint wrap (generally indicated by reference number 42), the associated joint may protrude through or otherwise be accommodated by the aperture 40. By so accommodating the joint, the magnetic joint wrap 42 surrounds and addresses the joint and allows for better articulation of the joint while the magnetic joint wrap 42 is wrapped about it.

As shown in FIG. 2, attachment elements provide means by which the magnetic joint wrap 42 may be attached to or about the joint. Particularly, in one embodiment, hook and loop fasteners such as that marketed under the trade name of VELCRO® may be used to provide detachable attachment means by which the magnetic joint wrap 42 may be attached to the joint and its adjacent tissue or anatomical structures.

As shown in FIG. 2, a first attachment element 50 has a corresponding and oppositely opposed attachment element 52 on a same side of the magnetic joint wrap 42. Both attachment elements 50, 52 take the form of strips or projections that serve to adjustably and attachably engage a second attachment element 54 at the opposite side of the magnetic joint wrap. The exterior of the second attachment element 54 may be a hook portion of the hook and loop fastener while the interior or facing portions of the first attachment elements 50, 52 (portions that would face the second attachment element 54 when serving to attach the magnetic joint wrap 42), may be hook portions of a hook and loop fastener. Alternatively, snaps, buttons, or other means by which non-destructive and detachable fixation may be made between the two ends of the magnetic joint wrap 42 may be achieved may also be used to good advantage.

Figure 3:
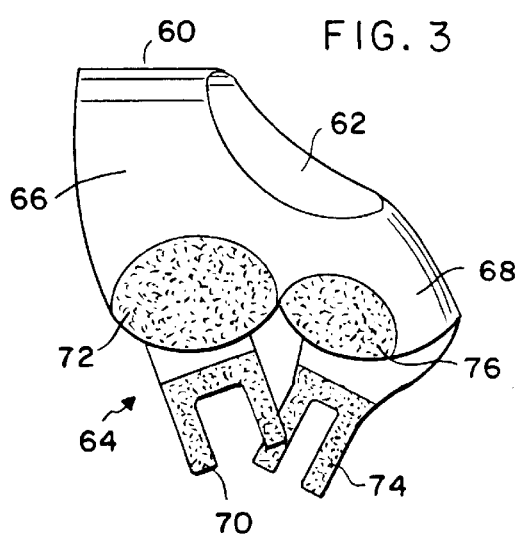
FIG. 3 shows a perspective view of a left shoulder wrap or ankle wrap.
Figure 4:
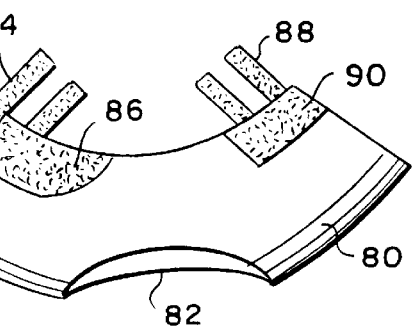
FIG. 4 shows a side perspective view of an elbow or knee wrap.
Figure 5:
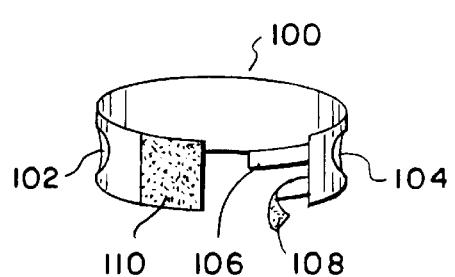
FIG. 5 shows a side perspective view of a hip, wrist, or ankle wrap.

Alternative embodiments of the magnetic joint wrap 42 of the present invention are shown in FIGS. 3–5 whereby specific joints may be accommodated by specific tailoring of the magnetic joint wrap 42 to the joint and its surrounding tissue.

In FIG. 3, a magnetic joint wrap 60 for the left shoulder is shown. The aperture for the left should joint wrap 60 is indicated by a reference number 62. The shoulder aperture 62 serves to provide means by which the shoulder may better engage the magnetic shoulder wrap 60. In an alternative embodiment, not shown, a shoulder aperture 62 may be absent and the entire shoulder may be covered. As can be seen in FIG. 3, distributed attachment means 64 are shown by which the magnetic shoulder wrap 60 may be attached both to the person's upper torso and the arm associated with the shoulder.

Projecting loop means 70, 74 such as those used in the magnetic joint wrap 42 as shown in FIG. 2 can likewise be used in the embodiments shown in FIG. 3. While the shoulder fits within the aperture 62, the upper torso is wrapped by a first portion 66 of the magnetic joint wrap 60 while the left arm is wrapped by a second portion 68. Torso attachment means 70, 72 may include VELCRO® or hook and loop fasteners so that the facing portions of the torso attachment elements 70, 72 when facing each other wrap around the upper left torso of a person.

The torso attachment means 70, 72 serve to adjustably and detachably engage one another to affix the magnetic shoulder joint wrap 60 of the present invention to the upper left torso of the person. In order to better attach the remaining arm portion 68 of the left shoulder magnetic joint wrap of FIG. 3 to the person, similar arm attachment means 74, 76 are used to attach the second arm portion 68 of the magnetic shoulder joint wrap 60 to the upper left arm or bicep of the person. Similar means may be used for the arm attachment elements 74, 76 as for the torso attachment elements 70, 72. In this way, adjustable and attachable means by which the left shoulder magnetic joint wrap 60 of FIG. 3 may be attached to the left shoulder of a person may be achieved. Such attachment is shown in FIG. 1 and is generally indicated at 30.

The embodiment of the present invention accommodating the right shoulder of a person may be achieved by generally creating a mirror image of the left shoulder magnetic joint wrap 60 as shown in FIG. 3.

In FIG. 4, an elbow or knee wrap 80 is shown. The optional aperture 82 therein serves to accommodate either a knee for larger versions of the embodiment shown in FIG. 4 or an elbow for smaller versions of the embodiment shown in FIG. 4. Certain accommodations may also be made for the skeleto-muscular structure adjacent both the knee and the elbow for the corresponding embodiments. However, generally, it appears that the configuration shown in FIG. 4 is applicable to both knees and elbows.

The attachment elements 84, 86, 88, 90 that serve to hold the knee/elbow wrap 80 to the associated limb are generally the same as shown in FIGS. 2 and 3 with VELCRO® hook and loop fasteners forming one embodiment that is complemented by other means of attachment such as snaps, buttons, or other adjustably attachable fabric fixation means.

As shown in FIG. 5, a wrist or hip wrap 100 (along the lines of that shown in FIG. 2) may optionally have dual apertures 102, 104 to accommodate oppositely opposed joint protuberances. Attachment elements 106, 108 serve to detachably attach to the corresponding attachment element 110 at the opposite end of the magnetic joint wrap 100.

Figure 6:
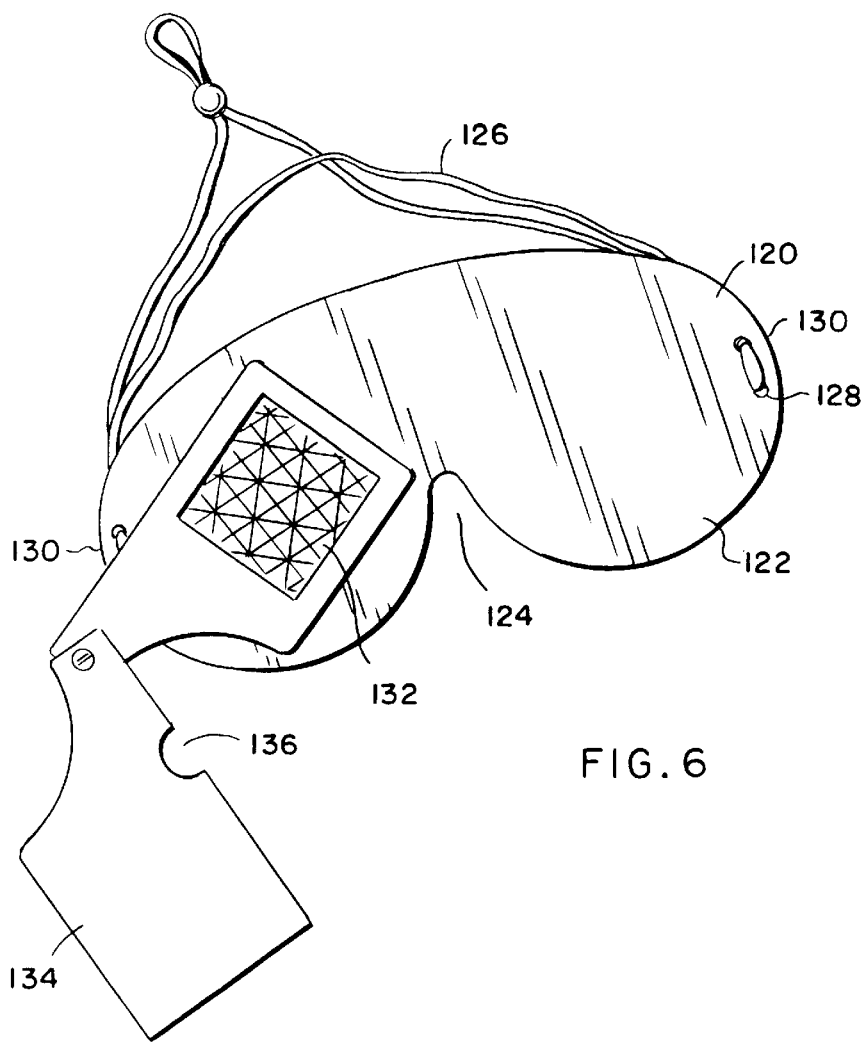
FIG. 6 shows a front perspective view of the eye mask of the present invention. A magnetic field indicator is shown adjacent the eye mask, indicating a first embodiment of a magnetic configuration.
Figure 7:
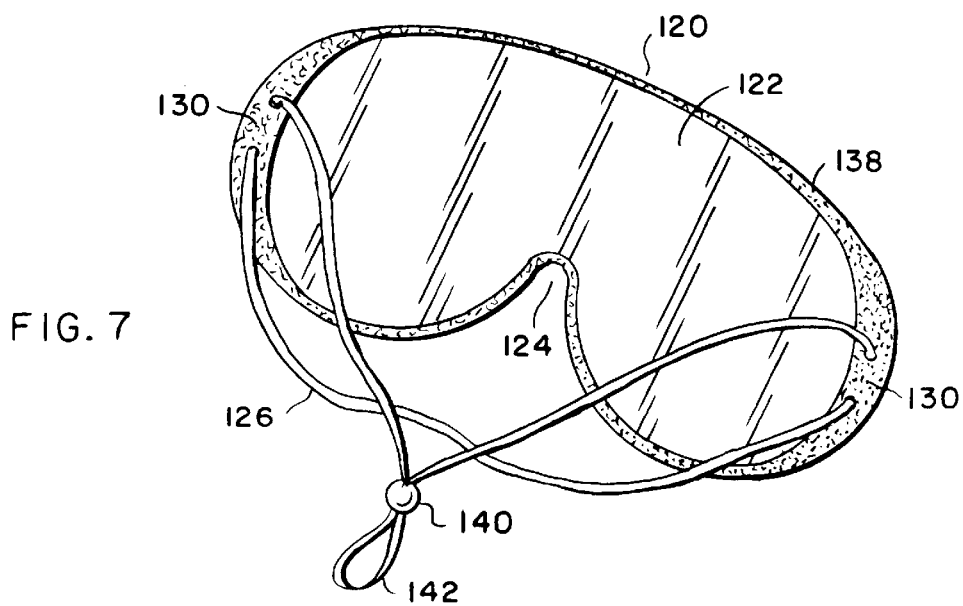
FIG. 7 shows a rear perspective view of the eye mask of FIG. 6.
Figure 8:
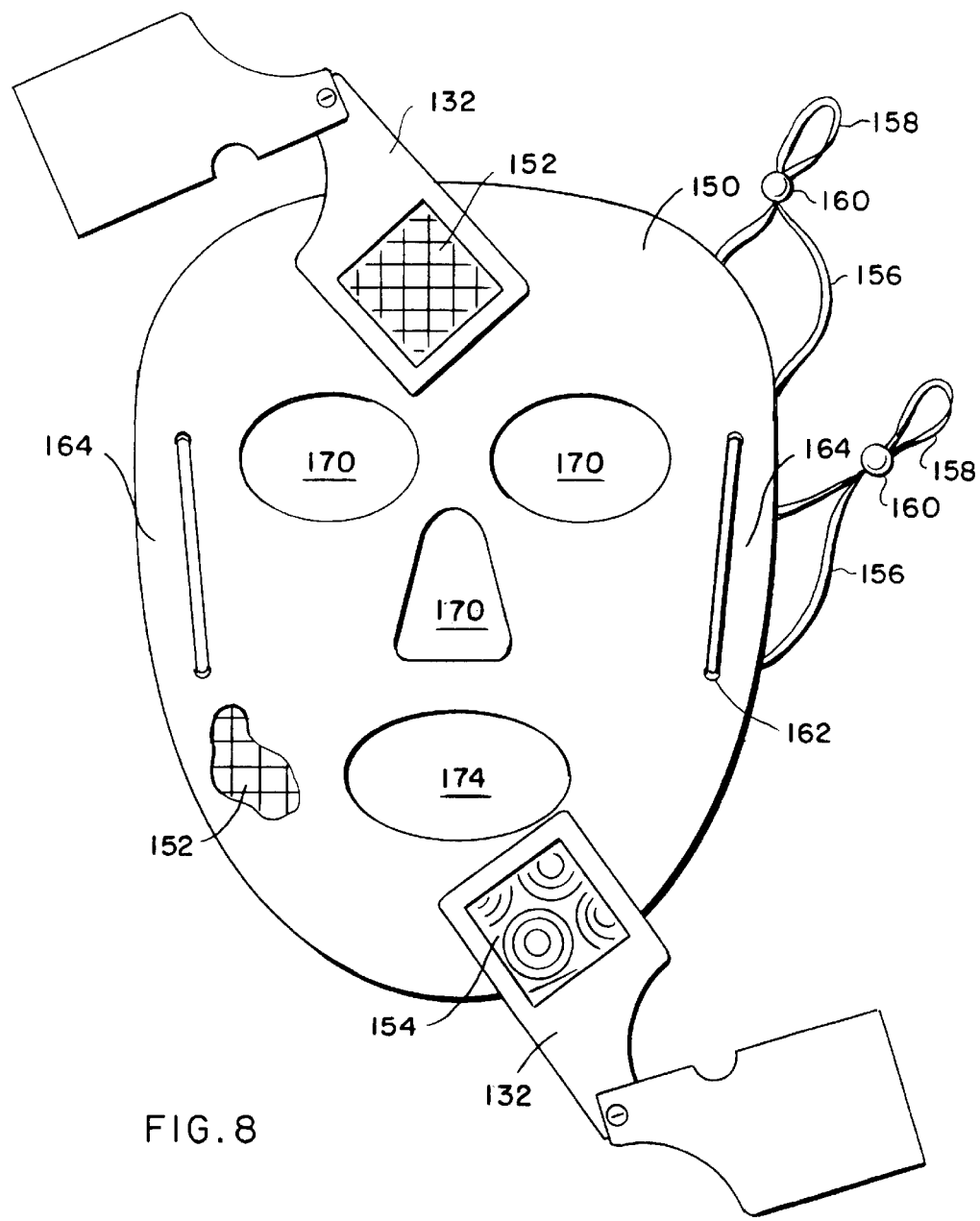
FIG. 8 shows a front perspective view of the face mask of the present invention with two magnetic indicators showing two alternative embodiments of the magnetic configuration used in the present invention.
Figure 9:
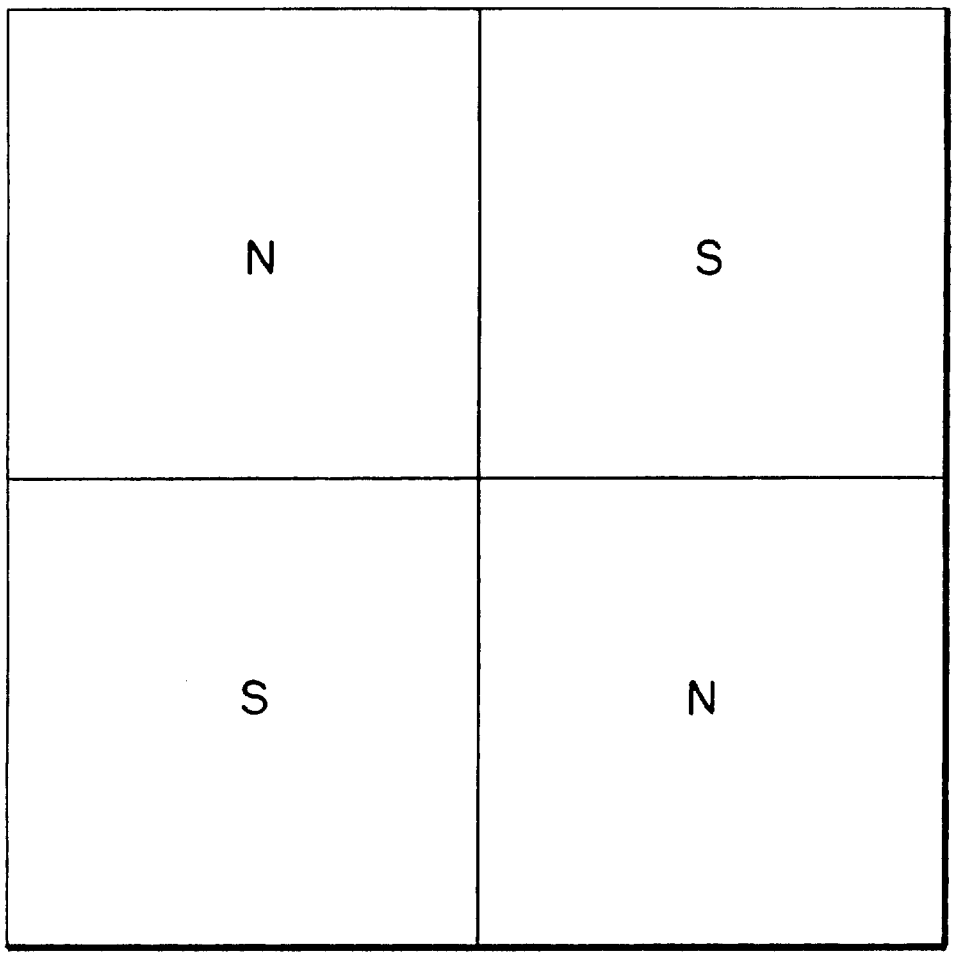
Figure 11:
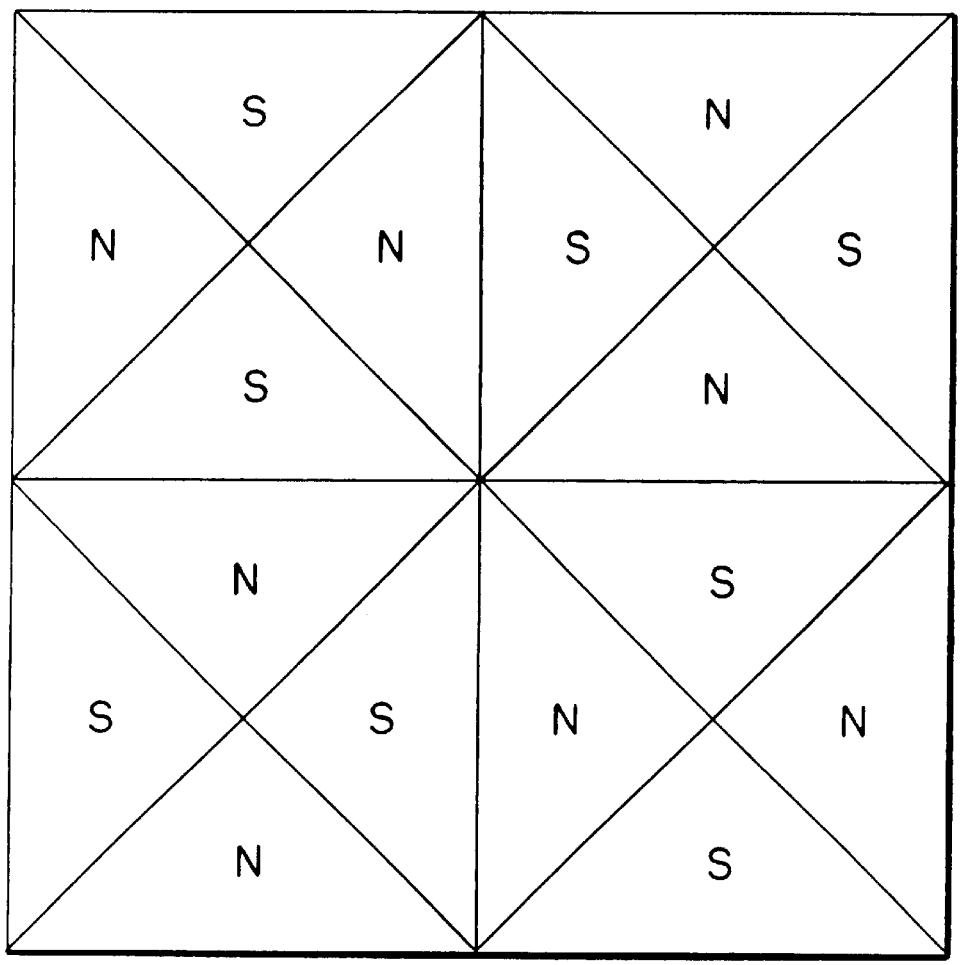
FIGS. 11 and 12 show a triangular checkerboard magnet configuration for use in the present invention.
Figure 12:
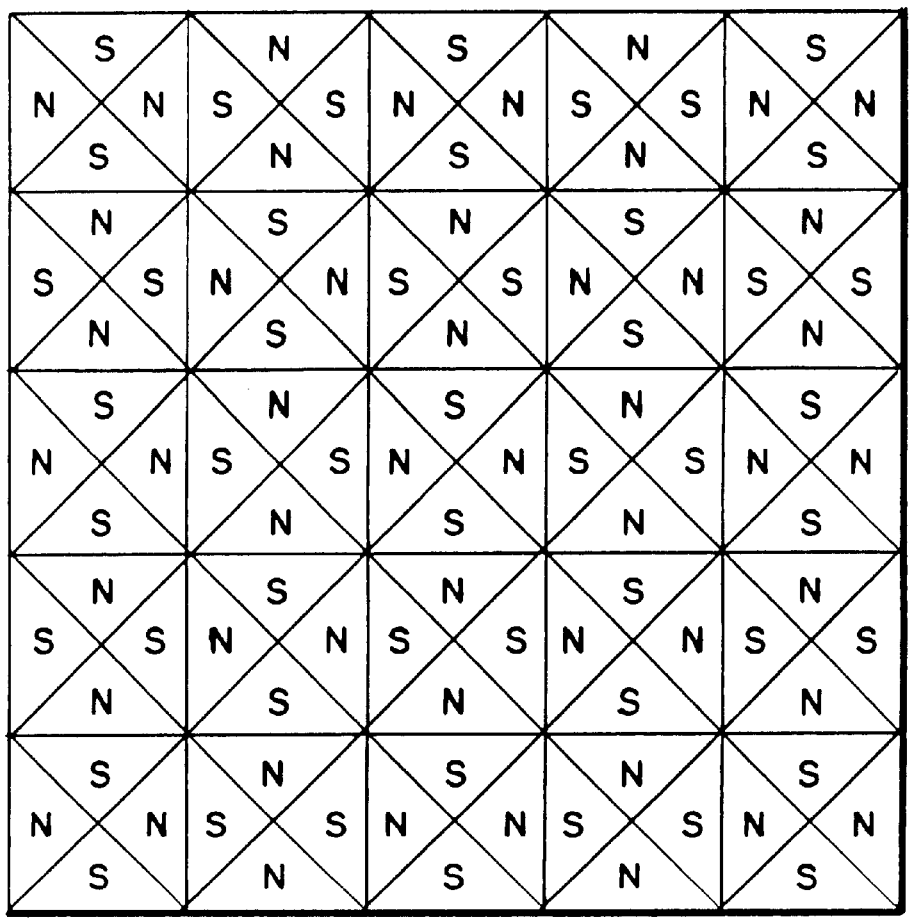
Figure 13:
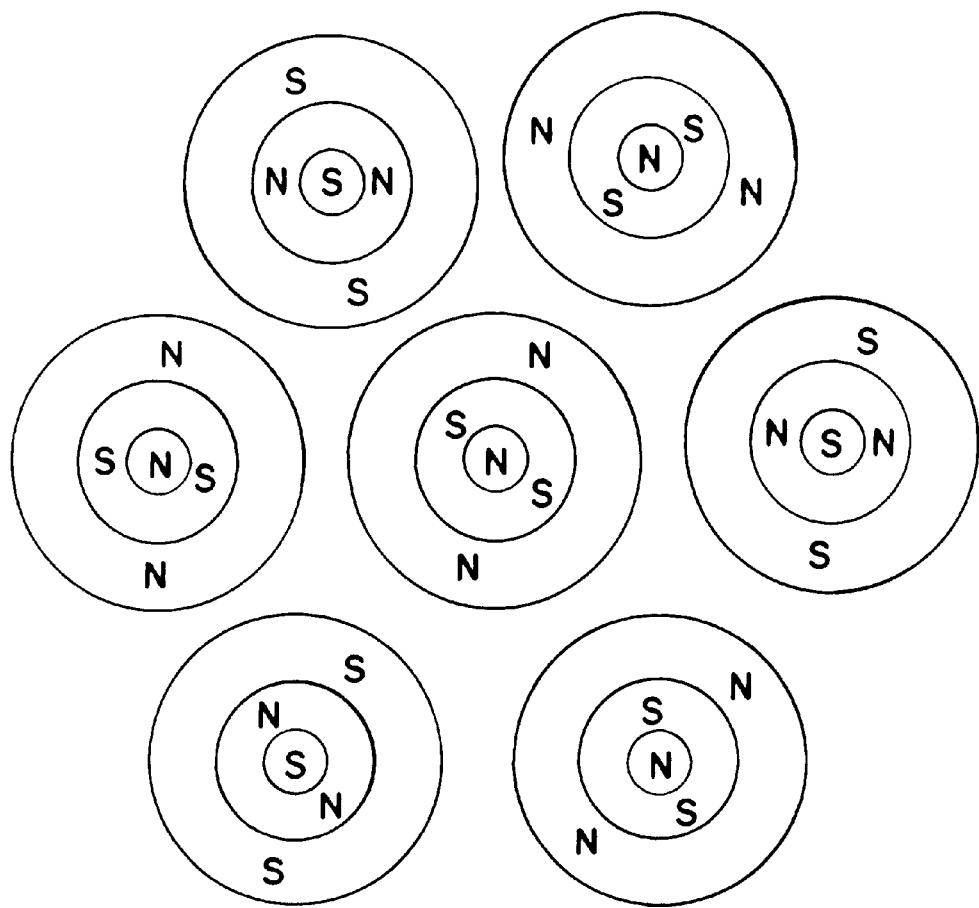
FIG. 13 shows a circular and toroidal magnet configuration for use in the present invention.

All the magnetic joint wraps shown in FIGS. 1–5, as well as the eye and face masks of FIGS. 6–8, all incorporate strong static magnets and/or magnetic compounds in order to provide strong magnetic fields. By means of such magnetic fields, effective magnetotherapy may be applied to the adjacent tissues. Recently, magnets having very strong magnetic properties have been recently developed. Particularly, neodymium iron boron (NdFeB or Nd—Fe—B) magnets provide very strong magnetic fields in the form of a permanent magnet. Such magnetism is well preserved and maintained at room temperatures that are well below the Curie temperatures for these magnets. Additionally, strong magnets such as ALNICO or ceramic magnets may be used so long as the flexibly elastic properties of the magnetic wrap are maintained. However, NdFeB magnets are advantageously used in the present situation as they provide the strongest magnetic fields for magnetotherapeutic purposes.

As indicated by trade materials published by Stanford Materials of San Mateo, Calif., the maximum energy product (BH max) of NdFeB magnets can easily reach 30 MGOe (megaGauss Oersted) and even go up to 48 MGOe for some magnets. The use of such magnetic materials for use in conjunction with static magnetism magnetotherapy is apparently new to the art as are the joint wraps incorporating such magnetic joint wraps of the present invention have incorporate such magnetotherapeutic properties.

Alternatively, magnetic ferrite can be used to good effect instead of NdFeB magnets.

In order to enhance such magnetotherapeutic properties, especially for iron or electrolytic fluids passing in proximity to such strong magnetic fields, FIGS. 9–13 show a variety of magnet configurations to provide for alternating magnetic polarity as travel is made along the magnetic sheets forming the magnetic joint wraps 42, etc. of the present invention. By arranging for alternate polarity, changing magnetic fields are encountered by charged molecules or atoms passing sufficiently proximate to the magnetic joint wrap so as to be subject to its magnetic fields. It is known that such changing magnetic fields induce currents and will also serve to exert both repelling and attractive forces upon such charged molecules or atoms.

With the additional articulation of the adjacent joints associated with the joint wraps of the present invention, additional changes or alteration to the magnetic field configuration imposed upon the adjacent tissues should be experienced to give rise to even more alternating or changing polarity of the magnetic fields involved. For example, when a person walks with one of the magnetic joint wraps of the present invention (such as that shown in FIG. 4), the articulation of the knee wrapped with the magnetic joint wrap serves to change the configuration of the associated joint wrap to give rise to additional changes in the magnetic fields provided by the magnetic joint wrap. It could therefore be seen that use of the magnetic wrap of the present invention in athletic or casual activities may serve to enhance the magnetotherapeutic effects thereof.

In FIGS. 6–8, eye and face masks are shown which may incorporate strong NdFeB magnets or other flexibly elastic and strongly magnetic components. FIG. 6 shows an eye mask 120 having an opaque exterior portion 122 with a nose notch 124. An elastic band or the like 126 serves to adjustably hold the eye mask 120 to a person's face as the elastic band 126 may pass through apertures or holes 128 present at the sides 130 of the eye mask. As shown in FIG. 6, a magnetic indicator 132 indicates a magnetic configuration as incorporated by the eye mask 120 and as reflected by the pattern shown in FIGS. 11 and 12. The magnetic indicator 132 may have a protective case 134 having a notch 136 by which the indicator 132 is more easily pivoted away from the protective case.

As shown in FIG. 7, the interior portion of the eye mask 120 has the opaque exterior portion 122 providing an opaque interior portion 122 so that light may not pass through the opaque exterior portion 122. This keeps the confines of the eye mask 120 generally dark when it is affixed over a person's eyes. In order to space the opaque portion 122 away from the person's face, a foam rubber or other comfortable engaging surface 138 circumscribes the perimeter of the opaque portion 122 so as to space apart the opaque portion 122 away from the person's face. This generally keeps the opaque portion from interfering with batting eyelashes or the like which can be a distraction to the person wearing the eye mask 120.

As shown in FIG. 7, the eye mask ends 130 may have wider foam rubber portions that accommodate the sides of a person's face near the eyes. The foam rubber serves as a light-tight gasket that comfortably engages the portions of a person's face surrounding the eyes so as to prevent the transmission of light into the eye mask and onto the person's eyes. A bead or the like 140 may serve to adjustably restrict the length of the elastic band 126 so that it may be adjustably conformed to hold the eye mask 120 to a person's face. The bead 140 may form a secondary loop 142 that serves to eliminate the slack that would otherwise be present in the elastic band 126.

In FIG. 8, a face mask 150 incorporating the superstrong and alternating polarity magnetic structures of the present invention is shown. Magnetic indicators 132 serve to show the checkerboard 152 or series of concentric circles 154 of alternating magnets as is respectively shown in FIGS. 9 and 10 (for a checkerboard configuration 152) and FIG. 13 (for the series of concentric circle configuration 154). The face mask 150 may also use elastic bands 156 with loops for taking up slack 158 created by the adjustable use of adjustment beads 160. The adjustable elastic bands 156 may pass through apertures 162 present at the sides 164 of the face mask 150.

Apertures in the face mask 150 may be present to accommodate the eyes 170, the nose 172, and the mouth 174. By providing a strongly magnetic face mask 150 as shown in FIG. 8 (constructed along the lines of the magnetic joint wraps described previously), magnetotherapeutic treatment may be effectively applied to a person's face for significant periods of time, particularly those during periods of sleep.

In order to achieve the flexibly stretchable and soft-to-the-touch material preferably used in the present invention, neoprene may be prepared with a magnetic ferrite filler, or, in the alternative, a neodymium-based magnetic filler. Caution should be used with neodymium-based substances as they have toxic properties. The amounts are set forth below are percentage by weight. However, these percentages may be crudely converted into parts per hundred rubber (PHR) by the using the percentage weight of neoprene to define one hundred parts per hundred.

Using a two-roll rubber mill as is known in the art, a slower roller is coated with neoprene while the entire roller structure is maintained in a cool condition as by a ten-ton chiller. The rollers may be approximately twenty inches (20") in diameter and sixty inches (60") in length. Once the neoprene has fully coated the slower roller, the magnetic ferrite or other strongly magnetic material may be fed into the highly viscous neoprene. The magnetic ferrite and other fillers are mixed into the highly viscous neoprene during the rolling process as it is fed into the nip, or bank, formed between the upper and faster spinning roller and the lower and slower turning roller. In addition to the magnetic ferrite or other strongly magnetic material, stearic acid, a complex fatty acid such as that known currently in the trade as INT-21G as manufactured by Axel Plastics Research Laboratories, of Woodside, N.Y., and zinc oxide curatives may be mixed in. The percentages by weight of these materials are as follows:

| Substances | Percentage By Weight | PHR |
|---|---|---|
| neoprene WRT | 26.9% | 100 |
| Magnetic Ferrite | 70.0% | 260.22 |
| Stearic Acid | 0.20% | 0.74 |
| INT-21G | 1.5% | 5.58 |
| Zinc oxide curatives | 1.4% | 5.20 |

In mixing the filler into the rolling neoprene, it is important to ensure that the INT-21G is not mixed in prematurely as it has a tendency to increase the viscosity of the rolling neoprene beyond that which is effective for working. Consequently, it is better to work in the magnetic ferrite first before adding too much of the INT-21G. One means by which this can be effected is by loading the feeder with the magnetic ferrite and then on top of the magnetic ferrite, adding the INT-21G, possibly with the stearic acid and zinc oxide curatives.

The neoprene is then worked into a sufficiently mixed condition. The rollers are then stopped and "pigs" are pulled off in strips and rolled up into a chilled calendar for pre-forming prior to pressing. Vulcanization then occurs during the pressing process which occurs at approximately two hundred (200) tons pressure and 350° F. It should be noted that the Du Pont neoprene WRT contains antioxidizing agents and the like to prevent oxidation of the magnetic ferrite. Additionally, the stearic acid helps to delay vulcanization so that it does not occur until intentionally induced during the pressing process. The zinc oxide curatives also help to cure the final product.

Figure 14:
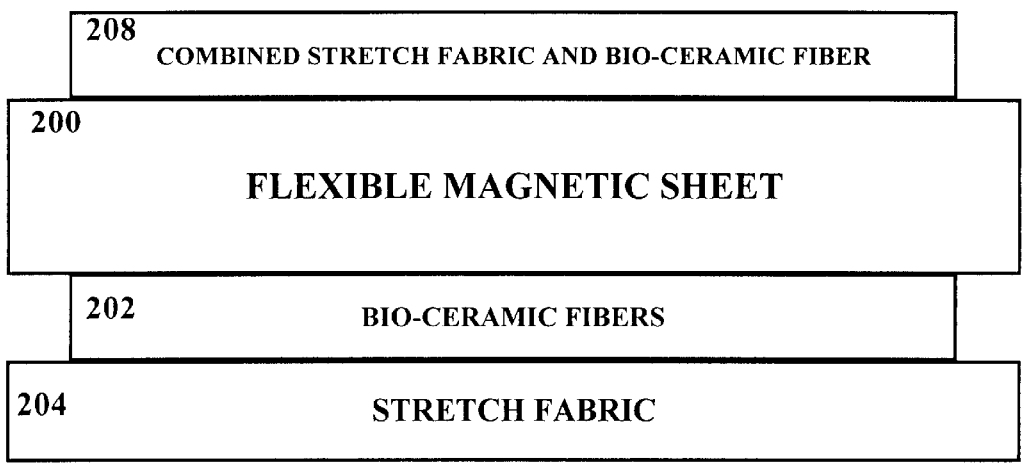
FIGS. 14 and 15 show side cross-sectional views of the wrap sheet used in the present invention. The dotted line in FIG. 15 indicates the optional separation of bio-ceramic fibers from the stretch fabric.
Figure 15:
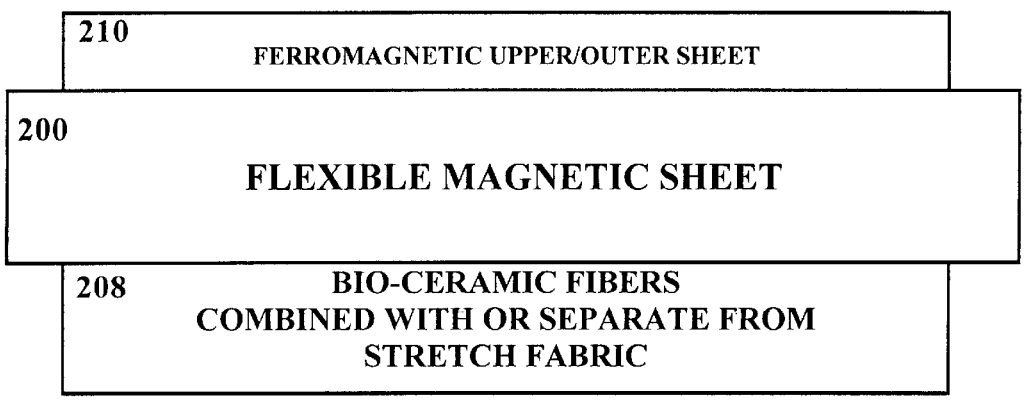

Once the pressing step has occurred, the resulting magnetizable and flexibly stretchable elastic sheet is then subject to lamination where glue is applied and then a stretchable fabric is applied to the stretchable elastic sheet to make it soft to the touch. The elasticity or stretchability of the applied fabric should be sufficient to accommodate the elastic and/or stretchable limits reasonably attained by the flexible and elastic magnetizable sheet. The stretchable fabric may incorporate far-infrared emitters, including bio-ceramic fibers, to provide far-infrared therapeutic capacity (FIGS. 14 and 15). Alternatively, a layer of far-infrared emitting fabric may be placed between the stretchable fabric and the flexible magnetic sheet (FIG. 14).

In a less preferred but alternative embodiment, the following components were used in units of parts per hundred rubber (PHR).

| Component | PHR |
|---|---|
| Royalene 552 | 55.00–45.00 |
| Nordel 2744 | — |
| Vistanex L-140 | 45.00–55.00 |
| CAPOW L-38H | 3.75 |
| CAPOW L-12H | 1.25 |
| SINO AM. P-4 | 1,250.00 |
| Ethanox 330 | 1.50 |
| AC 617A | 1.50 |
| "Zic Stick 85" | 3.00 |
| Stearic Acid | 0.75 |
| Altax (MBTs) | 0.30 |
| Methyl Tuads (TMTD) | 0.50 |
| Sulfur | 0.50 |
| PVI (Santogard/Vangard) | Optional |

The Royalene 552 is the Uniroyal brand of EPDM and may possibly be substituted by a Royalene 7200. These and other plastics are commonly available in pellet form. The Nordel 2744 may also act as a substitute for the Royalene 552 and is Du Pont's brand of EPDM. The Vistanex L-140 is a polyisobutylene compound available through Exxon. CAPOW L-38H and L-12H are organometallic couplers that are optionally used, but are preferred. SINO AM. P-4 is a lean neodymium magnetic filler used to confer magnetics properties to the resulting magnetic flexibly elastic magnetic sheet. Ethanox 330 is an antioxidant available through Ethyl Corporation. AC 617A is a polyethylene wax available through Allied-Signal. "Zic Stick 85" is a zinc oxide curative medium. The stearic acid is preferably of triple-pressed grade. The Altax, Methyl Tuads, and Sulfur are best added in a predispersed form and operate with the "Zic Stick 85," stearic acid, Altax (MBTS), Methyl Tuads (TMTD), and PVI (Santogard/Vangard) in order to effect a curing compound or mixture for the EPDM (ethylene/propylene/diene terpolymer).

One marketing channel for the Vistanex L-140 is R. T. Vanderbilt of Norwalk, Conn. The organometallic coupling agents (neoalkoxytitanates) are manufactured and sold by Kenrick Petrochemicals, Bayonne, N.J.

In order to mix this alternative formulation, a mill is used. When mill mixing, warm mill rolls should be used initially. The Vistanex is initially banded about one roller using a tight mill gap. The EPDM is then added and blended with the Vistanex. Coupling agents are added and blended with the banded materials. Slow addition of the P-4 neodymium compound is made with cool water turned on to cool the mill rollers. The mill gap is gradually opened as the P-4 incorporates into the binder thus increasing the batch volume. The polyethylene wax (AC 617A) can be added with the P-4 at the beginning of the addition process. The same is similarly true for the stearic acid. The rest of the curing mixture is then added at the end of the P-4 addition step.

The components are blended and distributed throughout the batch as quickly as possible. The mill is slabbed off and the sheets are cooled on a flat surface as soon as possible. The mill gap is then reset with warm rollers and resheeted with Vistanex to begin the process again. An additional variation of the process includes reducing the P-4 and/or increasing the Vistanex ratio.

In order to provide far-infrared stimulation of tissues, all embodiments of the present invention incorporate or provide far-infrared transmission properties. Bio-ceramic fibers may be used to provide such far-infrared transmission capacity. However, other means might be used to provide far-infrared transmission.

FIGS. 14 and 15 show different cross-sectional views of the magnetotherapeutic and bio-ceramic (far-infrared wave) fabric structure used to achieve the present invention.

The strong magnetic sheet 200 provides the magnetotherapy present in the present invention. The magnetic sheet 200 may be made of neodymium (Nd) or the like as described herein.

Adjacent the magnetic sheet 200 is a woven mat or other structure of bio-ceramic fibers 202 such as those marketed by 3M™ under the Nextel™ trademark. Nextel™ 312 fabric provides good far infrared (FIR) emittance in the 8–14 micron wavelength range. The Nextel™ 312 fabric is made up of crystals less than 500 nanometers large of $9Al_2O_3:2B_2O_3$+amorphous $SiO_2$. When the bio-ceramic fibers 202 are warmed by placement adjacent to the body, the far-infrared emittance may increase, providing greater far-infrared treatment in the 8–14 micron wavelength range.

Adjacent the bio-ceramic fibers 202 may be the stretch fabric layer 204. The stretch fabric layer 204 may serve to protect the far-infrared emitting layer 202. The far-infrared emitting layer 202 may also be flexible and stretchable. Alternatively, far-infrared emitters may be incorporated by the stretchable fabric 208.

Neodymium material is currently known to provide a powerful magnetic material. The present invention may provide a maximum field extension normal to its planar surface of approximately 3 inches with a field strength of 1.5 gauss at that distance. This is 6 times the field extension of a regular magnet known in the art. The maximum field strength at the surface of the present invention may be in excess of 2000 gauss.

An exterior or outer-side flexible and stretchable stainless steel or other metal sheet 210 may provide electromagnetic strength to the side applied to the body and limit the magnet effects of the present invention on the side of the wrap or mark away from the body. This metal fabric cover 210 may provide a surface upon which a company logo or the like may be displayed.

When the magnetotherapeutic device with the bio-ceramic fibers of the present invention is put to use, the heat from the body raises the temperature of the adjacent bio-ceramic fibers 202, 208 through the fabric 204, 208 or otherwise. The warmed bio-ceramic fibers 202 emit light in the far-infrared spectrum, preferably along the 8–14 micron wavelength range. The strong neodymium or other magnetic sheet 200 permeates the adjacent tissue with the available magnetic field, subjecting such tissue to magnetotherapy while the far-infrared emitters transmit, or emit, far-infrared light to simultaneously subject the same tissue to far-infrared treatment.

By providing a double-barreled approach whereby both magnetotherapy and far-infrared therapy are simultaneously provided, the present invention provides means by which better tissue therapy may be provided by both methods or treatment regimes. There may be some synergistic functions provided in the simultaneous application of both magnetotherapy, even strong magnetotherapy, and far-infrared wave treatment.

While the present invention has been described with regards to particular embodiments, it is recognized that additional variations of the present invention may be devised without departing from the inventive concept. For example, far-infrared emitters may be incorporated into the flexible magnetic sheet if performance is not impaired. Should a material that is both strongly magnetic and a far-infrared emitter be discovered, that material may form the basis for the flexible magnetic sheet.

What is claimed is:

1. A far-infrared emitting and magnetotherapeutic wrap for joints, comprising:
   a sheet of magnetic material defining an aperture;
   said aperture accommodating a joint;
   a far-infrared emitter cover coupled to said sheet;
   a first attachment element coupled to a first side of said sheet; and
   a second attachment element coupled to a second side of said sheet, said second attachment element detachably attaching to said first attachment element to adapt said sheet to a limb or member adjacent said joint; whereby far-infrared waves may be transmitted to said joint and said joint is adaptably engageable by said aperture with said sheet adapted to be wrapped about said joint adjacent said joint to supply attachably detachable far-infrared magnetotherapy to said joint, said aperture allowing better articulation of said joint when said sheet is wrapped about said joint.

2. The far-infrared emitting and magnetotherapeutic wrap for joints of claim 1, wherein said sheet of magnetic material further comprises:
   a flexible and elastic sheet of magnetic material, said sheet conforming to said joint when wrapped about said joint.

3. The far-infrared emitting and magnetotherapeutic wrap for joints of claim 2, wherein said flexible and elastic sheet of magnetic material further comprises magnetic materials to provide a magnetic field adjacent said joint, said magnetic materials selected from the group consisting of:
   neodymium-based magnetic materials and magnetic ferrite.

4. The far-infrared emitting and magnetotherapeutic wrap for joints of claim 2, wherein said flexible and elastic sheet of magnetic material comprises approximately:

| Substances | Percentage By Weight | PHR |
| --- | --- | --- |
| Neoprene | 26.9% | 100 |
| Magnetic Ferrite | 70.0% | 260.22 |
| Stearic Acid | 0.20% | 0.74 |
| INT-21G | 1.5% | 5.58 |
| Zinc oxide curatives | 1.4% | 5.20. |

5. The far-infrared emitting and magnetotherapeutic wrap for joints of claim 1, wherein said aperture is adapted to accommodate joints selected from the group consisting of: ankles, knees, hips, wrists, elbows, shoulders, and necks.

6. The far-infrared emitting and magnetotherapeutic wrap for joints of claim 1, wherein said sheet of magnetic material further comprises:
   a sheet of magnetic material having alternating magnetic polarity.

7. The far-infrared emitting and magnetotherapeutic wrap for joints of claim 6, wherein said sheet of magnetic material having alternating magnetic polarity comprises planar alternating magnetic means whereby travel in any direction along said sheet of magnetic material provides alternating magnetic polarity.

8. The far-infrared emitting and magnetotherapeutic wrap for joints of claim 7, wherein alternating magnetic polarity of said sheet of alternating magnetic polarity material is selected from the group consisting of:
   alternating magnetic triangles, alternating magnetic squares, and series of alternating concentric circles.

9. The far-infrared emitting and magnetotherapeutic wrap for joints of claim 1, wherein said far-infrared emitter cover comprises bio-ceramic fiber.

10. A far-infrared emitting and magnetotherapeutic wrap for joints, comprising:
   a flexible and elastic sheet of magnetic material having alternating magnetic polarity incorporating magnetic material to provide a magnetic field;
   said sheet defining an aperture accommodating a joint;
   said sheet adapted to conform to said joint when wrapped about said joint;
   a far-infrared emitter cover coupled to said sheet;
   a first attachment element coupled to a first side of said sheet; and
   a second attachment element coupled to a second side of said sheet, said second attachment element detachably attaching to said first attachment element to adapt said sheet to a limb or member adjacent said joint; whereby
   said joint may be subject to far-infrared therapy and said joint may be accommodated by said aperture with said sheet wrapped about said joint adjacent said joint to supply attachably detachable far-infrared magnetotherapy to said joint, said aperture allowing better articulation of said joint when said sheet is wrapped about said joint.

11. The far-infrared emitting and magnetotherapeutic wrap for joints of claim 10, wherein said flexible and elastic sheet of magnetic material comprises approximately:

| Substances | Percentage By Weight | PHR |
| --- | --- | --- |
| Neoprene | 26.9% | 100 |
| Magnetic Ferrite | 70.0% | 260.22 |
| Stearic Acid | 0.20% | 0.74 |
| INT-21G | 1.5% | 5.58 |
| Zinc oxide curatives | 1.4% | 5.20. |

12. The far-infrared emitting and magnetotherapeutic wrap for joints of claim 10, wherein said aperture is adapted to accommodate joints selected from the group consisting of:
   ankles, knees, hips, wrists, elbows, shoulders, and necks.

13. The far-infrared emitting and magnetotherapeutic wrap for joints of claim 10, wherein said flexible and elastic sheet of magnetic material further comprises magnetic materials to provide a magnetic field adjacent said joint, said magnetic materials selected from the group consisting of:
   neodymium-based magnetic materials and magnetic ferrite.

14. The far-infrared emitting and magnetotherapeutic wrap for joints of claim 10, wherein said sheet of magnetic material having alternating magnetic polarity comprises planar alternating magnetic means whereby travel in any direction along said sheet of magnetic material provides alternating magnetic polarity.

15. The far-infrared emitting and magnetotherapeutic wrap for joints of claim 14, wherein alternating magnetic polarity of said sheet of alternating magnetic polarity material is selected from the group consisting of:
   alternating magnetic triangles, alternating magnetic squares, and series of alternating concentric circles.

16. The far-infrared emitting and magnetotherapeutic wrap for joints of claim 10, wherein said far-infrared emitter cover comprises bio-ceramic fiber.

17. A magnetic magnetotherapeutic and far-infrared mask for treating tissue of a person's face, comprising:
   an opaque eye mask adapted to cover the eyes of the person's face and preventing light from illuminating the person's eyes;
   an opaque perimeter cushion circumscribing a perimeter of said eye mask, said perimeter cushion adapted to hold said eye mask slightly away from the person's face for the person's greater comfort, said perimeter cushion adapted to provide a light-tight seal between said eye mask and the person's face so that the person's eyes are held in darkness by the magnetic mask;
   magnetic planar alternating magnetic means for providing changes in magnetic polarity, said alternating magnetic means coupled to said eye mask, travel in any direction in a plane of said alternating magnetic means providing alternating magnetic polarity;
   a far-infrared emitter cover, said far-infrared emitter cover coupled to said magnetic means; and
   an adjustable elastic band adapted to adjustably attach said eye mask to the face; whereby
   the person donning the magnetic mask may darken the face and eyes and simultaneously subject them to spatially alternating magnetic polarity and far-infrared waves consequently stimulating ferromagnetic ion-containing blood as it passes through changing magnetic fields as well as providing infra-red treatment.

18. The magnetic magnetotherapeutic and far-infrared mask for treating tissue of a person's face of claim 17, wherein said magnetic planar alternating magnetic means for providing changes in magnetic polarity is selected from the group consisting of:
   neodymium-based magnetic materials and magnetic ferrite.

19. The magnetic magnetotherapeutic and far-infrared mask for treating tissue of a person's face of claim 17, wherein said planar alternating magnetic means is selected from the group consisting of:
   alternating magnetic triangles, alternating magnetic squares, and series of alternating concentric circles.

20. The magnetic magnetotherapeutic and far-infrared mask for treating tissue of a person's face of claim 17, wherein said far-infrared emitter cover comprises bio-ceramic fiber.

21. A magnetic magnetotherapeutic and far-infrared mask for treating tissue of a person's face, comprising:
   a face mask defining openings or apertures for the person's eyes, nose, and mouth;
   magnetic planar alternating magnetic means for providing changes in magnetic polarity, said alternating magnetic means coupled to said face mask, travel in any direction in a plane of said planar alternating magnetic means providing alternating magnetic polarity;
   a far-infrared emitter cover, said far-infrared emitter cover coupled to said magnetic means; and
   an adjustable elastic band adapted to adjustably attach said face mask to the face; whereby
   the person donning the magnetic mask may cover the face and simultaneously subject it to spatially alternating magnetic polarity and far-infrared waves consequently stimulating ferromagnetic ion-containing blood as it passes through changing magnetic fields as well as providing far-infrared treatment.

22. The magnetic magnetotherapeutic and far-infrared mask for treating tissue of a person's face of claim 21, wherein said planar alternating magnetic means is selected from the group consisting of:

alternating magnetic triangles, alternating magnetic squares, and series of alternating concentric circles.

23. The magnetic magnetotherapeutic and far-infrared mask for treating tissue of a person's face of claim 21, wherein said magnetic planar alternating magnetic means for providing changes in magnetic polarity is selected from the group consisting of:

neodymium-based magnetic materials and magnetic ferrite.

24. The magnetic magnetotherapeutic and far-infrared mask for treating tissue of a person's face of claim 21, wherein said far-infrared emitter cover comprises bio-ceramic fiber.

* * * * *